US008897878B2

(12) United States Patent
Shuros

(10) Patent No.: US 8,897,878 B2
(45) Date of Patent: Nov. 25, 2014

(54) METHOD AND APPARATUS FOR GASTROINTESTINAL STIMULATION VIA THE LYMPHATIC SYSTEM

(75) Inventor: Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 178 days.

(21) Appl. No.: 12/775,223

(22) Filed: May 6, 2010

(65) Prior Publication Data
US 2010/0217346 A1 Aug. 26, 2010

Related U.S. Application Data

(62) Division of application No. 11/422,418, filed on Jun. 6, 2006, now Pat. No. 7,734,341.

(51) Int. Cl.
*A61N 1/36* (2006.01)

(52) U.S. Cl.
CPC .................................. *A61N 1/36007* (2013.01)
USPC .................................. 607/40; 607/2; 607/116

(58) Field of Classification Search
USPC ................................................ 607/2, 40, 116
See application file for complete search history.

(56) References Cited

U.S. PATENT DOCUMENTS

| | | | |
|---|---|---|---|
| 3,814,080 A | 6/1974 | Norman | |
| 3,902,501 A * | 9/1975 | Citron et al. | 607/126 |
| 3,916,875 A | 11/1975 | Toch | |
| 4,650,467 A | 3/1987 | Bonello et al. | |
| 4,792,330 A | 12/1988 | Lazarus et al. | |
| 4,909,787 A | 3/1990 | Danforth | |
| 4,957,484 A | 9/1990 | Murtfeldt | |
| 5,112,303 A | 5/1992 | Pudenz et al. | |
| 5,188,104 A | 2/1993 | Wernicke et al. | |
| 5,231,988 A * | 8/1993 | Wernicke et al. | 607/118 |
| 5,263,480 A | 11/1993 | Wernicke et al. | |
| 5,284,153 A | 2/1994 | Raymond et al. | |
| 5,300,107 A * | 4/1994 | Stokes et al. | 607/126 |

(Continued)

FOREIGN PATENT DOCUMENTS

| | | |
|---|---|---|
| EP | 1504778 A2 | 2/2005 |
| JP | 0355032 | 3/1991 |

(Continued)

OTHER PUBLICATIONS

U.S. Appl. No. 11/469,793, Final Office Action mailed Mar. 14, 2011, 7 pgs.

(Continued)

*Primary Examiner* — Niketa Patel
*Assistant Examiner* — Christopher A Flory
(74) *Attorney, Agent, or Firm* — Schwegman Lundberg & Woessner, P.A.

(57) ABSTRACT

An implantable gastrointestinal (GI) stimulation system includes an implantable medical device and at least one stimulus delivery device configured to be placed in one or more lymphatic vessels of a patient, such as the patient's thoracic duct and/or vessels branching from the thoracic duct. In one embodiment, the implantable medical device includes a GI stimulation circuit to deliver electrical stimulation pulses to one or more target regions adjacent to a lymphatic vessel through the stimulus delivery device. In one embodiment, to control obesity, the electrical stimulation pulses are delivered to the organs and/or nerves of the GI tract to create a sensation of satiety and/or to expedite food movement through the GI tract.

17 Claims, 7 Drawing Sheets

(56) References Cited

U.S. PATENT DOCUMENTS

| | | |
|---|---|---|
| 5,305,745 A | 4/1994 | Zacouto |
| 5,333,609 A | 8/1994 | Bedingham et al. |
| 5,387,231 A | 2/1995 | Sporer |
| 5,391,143 A | 2/1995 | Kensey |
| 5,423,872 A | 6/1995 | Cigaina |
| 5,500,005 A | 3/1996 | Strandberg et al. |
| 5,596,988 A | 1/1997 | Markle et al. |
| 5,655,548 A | 8/1997 | Nelson et al. |
| 5,658,318 A | 8/1997 | Stroetmann et al. |
| 5,817,138 A | 10/1998 | Suzuki |
| 5,865,744 A | 2/1999 | Lemelson |
| 5,891,084 A | 4/1999 | Lee |
| 6,024,704 A | 2/2000 | Meador et al. |
| 6,106,477 A | 8/2000 | Miesel et al. |
| 6,115,637 A | 9/2000 | Lennox et al. |
| 6,129,685 A | 10/2000 | Howard, III |
| 6,238,423 B1 | 5/2001 | Bardy |
| 6,272,370 B1 | 8/2001 | Gillies et al. |
| 6,292,695 B1 | 9/2001 | Webster, Jr. et al. |
| 6,321,109 B2 | 11/2001 | Ben-Haim et al. |
| 6,347,247 B1 | 2/2002 | Dev et al. |
| 6,368,274 B1 | 4/2002 | Van Antwerp et al. |
| 6,370,417 B1 | 4/2002 | Horbaschek et al. |
| 6,475,223 B1 | 11/2002 | Werp et al. |
| 6,535,764 B2 | 3/2003 | Imran et al. |
| 6,542,776 B1 | 4/2003 | Gordon et al. |
| 6,584,362 B1 | 6/2003 | Scheiner et al. |
| 6,587,719 B1 | 7/2003 | Barrett et al. |
| 6,606,523 B1 | 8/2003 | Jenkins |
| 6,609,025 B2 | 8/2003 | Barrett et al. |
| 6,611,715 B1 | 8/2003 | Boveja |
| 6,615,084 B1 | 9/2003 | Cigaina |
| 6,629,534 B1 | 10/2003 | St. Goar et al. |
| 6,676,686 B2 | 1/2004 | Naganuma |
| 6,678,557 B1 | 1/2004 | Tumey |
| 6,684,104 B2 | 1/2004 | Gordon et al. |
| 6,692,490 B1 * | 2/2004 | Edwards .................... 606/41 |
| 6,735,477 B2 * | 5/2004 | Levine ....................... 607/58 |
| 6,741,882 B2 | 5/2004 | Schaffter et al. |
| 6,804,558 B2 | 10/2004 | Haller et al. |
| 6,826,428 B1 | 11/2004 | Chen et al. |
| 6,835,194 B2 | 12/2004 | Johnson et al. |
| 6,865,416 B2 | 3/2005 | Dev et al. |
| 6,879,859 B1 | 4/2005 | Boveja |
| 6,889,076 B2 | 5/2005 | Cigaina |
| 6,893,429 B2 | 5/2005 | Petersen |
| 6,895,278 B1 | 5/2005 | Gordon |
| 6,912,419 B2 * | 6/2005 | Hill et al. .................... 607/9 |
| 6,918,873 B1 | 7/2005 | Millar et al. |
| 6,950,707 B2 | 9/2005 | Whitehurst |
| 6,970,741 B1 | 11/2005 | Whitehurst |
| 6,974,448 B2 | 12/2005 | Petersen |
| 7,167,751 B1 * | 1/2007 | Whitehurst et al. ........... 607/40 |
| 7,250,041 B2 * | 7/2007 | Chiu et al. ................... 604/523 |
| 7,295,877 B2 | 11/2007 | Govari |
| 7,317,941 B2 | 1/2008 | Stomberg et al. |
| 7,526,337 B2 | 4/2009 | Shuros et al. |
| 7,606,622 B2 | 10/2009 | Reeve |
| 7,616,991 B2 | 11/2009 | Mann et al. |
| 7,620,454 B2 * | 11/2009 | Dinsmoor et al. ............ 607/40 |
| 7,734,341 B2 | 6/2010 | Shuros |
| 7,747,334 B2 * | 6/2010 | Bly et al. ................... 607/122 |
| 7,769,427 B2 | 8/2010 | Shachar |
| 7,774,055 B1 | 8/2010 | Min |
| 7,873,401 B2 | 1/2011 | Shachar |
| 7,894,906 B2 | 2/2011 | Shuros |
| 7,966,057 B2 | 6/2011 | Macaulay |
| 8,116,883 B2 * | 2/2012 | Williams et al. ............ 607/120 |
| 8,126,538 B2 | 2/2012 | Shuros et al. |
| 8,369,943 B2 | 2/2013 | Shuros et al. |
| 2001/0007924 A1 | 7/2001 | Kamada et al. |
| 2001/0037061 A1 | 11/2001 | Eckmiller et al. |
| 2001/0041870 A1 | 11/2001 | Gillis et al. |
| 2002/0016615 A1 | 2/2002 | Dev et al. |
| 2002/0029037 A1 | 3/2002 | Kim |
| 2002/0072780 A1 | 6/2002 | Foley |
| 2002/0087192 A1 | 7/2002 | Barrett et al. |
| 2002/0123674 A1 | 9/2002 | Plicchi et al. |
| 2002/0156462 A1 | 10/2002 | Stultz |
| 2002/0188253 A1 | 12/2002 | Gordon et al. |
| 2003/0009202 A1 * | 1/2003 | Levine ....................... 607/58 |
| 2003/0018247 A1 | 1/2003 | Gonzalez |
| 2003/0036773 A1 | 2/2003 | Whitehurst et al. |
| 2003/0055463 A1 | 3/2003 | Gordon et al. |
| 2003/0078623 A1 | 4/2003 | Weinberg et al. |
| 2003/0105506 A1 | 6/2003 | Krishnan et al. |
| 2003/0113303 A1 | 6/2003 | Schwartz |
| 2003/0114895 A1 | 6/2003 | Gordon et al. |
| 2003/0144708 A1 | 7/2003 | Starkebaum |
| 2003/0204185 A1 | 10/2003 | Sherman et al. |
| 2004/0015193 A1 | 1/2004 | Lamson et al. |
| 2004/0015201 A1 | 1/2004 | Greenstein |
| 2004/0024428 A1 | 2/2004 | Barrett et al. |
| 2004/0039427 A1 | 2/2004 | Barrett et al. |
| 2004/0088022 A1 | 5/2004 | Chen |
| 2004/0102804 A1 | 5/2004 | Chin |
| 2004/0106953 A1 | 6/2004 | Yomtov et al. |
| 2004/0147976 A1 | 7/2004 | Gordon et al. |
| 2004/0158297 A1 | 8/2004 | Gonzalez |
| 2004/0162595 A1 | 8/2004 | Foley |
| 2004/0172080 A1 | 9/2004 | Stadler et al. |
| 2004/0172088 A1 * | 9/2004 | Knudson et al. ............. 607/40 |
| 2004/0172102 A1 | 9/2004 | Leysieffer |
| 2004/0193229 A1 | 9/2004 | Starkebaum et al. |
| 2004/0210118 A1 | 10/2004 | Letort |
| 2004/0230255 A1 | 11/2004 | Dobak, III |
| 2004/0243182 A1 * | 12/2004 | Cohen et al. ................. 607/2 |
| 2005/0033376 A1 | 2/2005 | Whitehurst |
| 2005/0043675 A1 | 2/2005 | Pastore et al. |
| 2005/0043765 A1 | 2/2005 | Williams et al. |
| 2005/0043894 A1 | 2/2005 | Fernandez |
| 2005/0049472 A1 | 3/2005 | Manda |
| 2005/0065575 A1 | 3/2005 | Dobak |
| 2005/0070974 A1 | 3/2005 | Knudson et al. |
| 2005/0075678 A1 | 4/2005 | Faul |
| 2005/0075701 A1 | 4/2005 | Shafer |
| 2005/0075702 A1 | 4/2005 | Shafer |
| 2005/0080346 A1 | 4/2005 | Gianchandani et al. |
| 2005/0080462 A1 | 4/2005 | Jenkins et al. |
| 2005/0090873 A1 | 4/2005 | Imran |
| 2005/0131486 A1 * | 6/2005 | Boveja et al. ................ 607/40 |
| 2005/0143765 A1 | 6/2005 | Bachmann et al. |
| 2005/0143787 A1 | 6/2005 | Boveja et al. |
| 2005/0149014 A1 | 7/2005 | Hauck et al. |
| 2005/0149141 A1 | 7/2005 | Starkebaum |
| 2005/0149142 A1 | 7/2005 | Starkebaum |
| 2005/0149157 A1 | 7/2005 | Hunter et al. |
| 2005/0187584 A1 | 8/2005 | Denker et al. |
| 2005/0222637 A1 | 10/2005 | Chen |
| 2005/0222638 A1 | 10/2005 | Foley et al. |
| 2005/0228471 A1 | 10/2005 | Williams et al. |
| 2005/0240239 A1 | 10/2005 | Boveja et al. |
| 2005/0240243 A1 | 10/2005 | Barolat et al. |
| 2005/0246006 A1 | 11/2005 | Daniels |
| 2005/0267440 A1 | 12/2005 | Herman et al. |
| 2005/0273060 A1 | 12/2005 | Levy et al. |
| 2005/0288729 A1 | 12/2005 | Libbus et al. |
| 2005/0288730 A1 | 12/2005 | Deem et al. |
| 2006/0020333 A1 | 1/2006 | Lashinski et al. |
| 2006/0030837 A1 | 2/2006 | McKenna et al. |
| 2006/0074453 A1 | 4/2006 | Kieval et al. |
| 2006/0149331 A1 | 7/2006 | Mann et al. |
| 2006/0167416 A1 * | 7/2006 | Mathis et al. ............ 604/164.01 |
| 2006/0217779 A1 | 9/2006 | Ransbury et al. |
| 2006/0247601 A1 | 11/2006 | Ellin et al. |
| 2006/0259077 A1 * | 11/2006 | Pardo et al. ................. 607/2 |
| 2007/0021731 A1 | 1/2007 | Garibaldi et al. |
| 2007/0027460 A1 | 2/2007 | Case et al. |
| 2007/0027484 A1 * | 2/2007 | Guzman et al. .............. 607/2 |
| 2007/0027500 A1 * | 2/2007 | Maschino et al. ............ 607/45 |
| 2007/0244520 A1 | 10/2007 | Ferren et al. |
| 2007/0255340 A1 | 11/2007 | Giftakis et al. |
| 2007/0270675 A1 | 11/2007 | Kane et al. |
| 2007/0282376 A1 | 12/2007 | Shuros |

(56) References Cited

U.S. PATENT DOCUMENTS

| | | |
|---|---|---|
| 2007/0282380 A1 | 12/2007 | Brooke et al. |
| 2007/0282382 A1 | 12/2007 | Shuros et al. |
| 2007/0282386 A1 | 12/2007 | Shuros |
| 2007/0282390 A1 | 12/2007 | Shuros |
| 2008/0009719 A1 | 1/2008 | Shuros et al. |
| 2008/0058887 A1 | 3/2008 | Griffin et al. |
| 2008/0086185 A1 | 4/2008 | Amurthur et al. |
| 2008/0097412 A1 | 4/2008 | Shuros et al. |
| 2008/0260861 A1 | 10/2008 | Hagendoorn et al. |
| 2008/0294228 A1 | 11/2008 | Brooke et al. |
| 2009/0228059 A1 | 9/2009 | Shuros |
| 2010/0042170 A1 | 2/2010 | Shuros et al. |
| 2010/0227807 A1 | 9/2010 | Stossel et al. |
| 2011/0106202 A1 | 5/2011 | Ding et al. |

FOREIGN PATENT DOCUMENTS

| | | |
|---|---|---|
| JP | 6-113998 A | 4/1994 |
| JP | 2004-065529 A | 3/2004 |
| JP | 2004-524893 A | 8/2004 |
| JP | 2005532878 A | 11/2005 |
| SU | 1074527 A1 | 2/1984 |
| WO | WO-93/14694 A1 | 8/1993 |
| WO | WO-9314694 A1 | 8/1993 |
| WO | WO-03028542 A2 | 4/2003 |
| WO | WO-03/098177 A2 | 11/2003 |
| WO | WO-03098177 A2 | 11/2003 |
| WO | WO-2004/006795 A1 | 1/2004 |
| WO | WO-2004/032791 A2 | 4/2004 |
| WO | WO-2005/089863 | 9/2005 |
| WO | WO-2005/089863 A1 | 9/2005 |
| WO | WO-2005107862 A1 | 11/2005 |
| WO | WO-2007/067690 A2 | 6/2007 |
| WO | WO-2007/146489 A2 | 12/2007 |
| WO | WO-2007/146493 A1 | 12/2007 |
| WO | WO-2007/146517 A2 | 12/2007 |
| WO | WO-2008/030344 A2 | 3/2008 |

OTHER PUBLICATIONS

U.S. Appl. No. 11/752,377, Non Final Office Action mailed Mar. 23, 2011, 10 pgs.
U.S. Appl. No. 12/430,211, Response filed Jun. 1, 2011 to Final Office Action mailed Feb. 1, 2011, 7 pgs.
U.S. Appl. No. 12/604,233, Advisory Action mailed May 3, 2011, 8 pgs.
U.S. Appl. No. 12/604,233, Response filed Apr. 12, 2011 to Final Office Action mailed Feb. 15, 2011 , 11 pgs.
European Application No. 07782375.5, Response filed May 11, 2011 to Office Action mailed Nov. 22, 2010, 6 pgs.
U.S. Appl. No. 11/422,414, Final Office Action mailed Feb. 5, 2010, 16 pgs.
U.S. Appl. No. 11/422,414, response filed May 5, 2010 to Final Office Action mailed Feb. 5, 2010, 6 pgs.
U.S. Appl. No. 11/422,414, response filed Dec. 14, 2009 to Non-Final Office Action mailed Aug. 14, 2009, 7 pgs.
U.S. Appl. No. 11/422,414, Non-Final Office Action mailed Aug. 14, 2009, 18 pgs.
U.S. Appl. No. 11/422,417, Non-Final Office Action mailed Sep. 25, 2007, 6 pgs.
U.S. Appl. No. 11/422,417, Non-Final Office Action mailed Apr. 21, 2008, 7 pgs.
U.S. Appl. No. 11/422,417, Response filed Aug. 21, 2008 to Non Final Office Action mailed Apr. 21, 2008, 6 pgs.
U.S. Appl. No. 11/422,417, Non-Final Office Action mailed Sep. 25, 2007, 7 pgs.
U.S. Appl. No. 11/422,417, Response filed Jan. 25, 2008 to Non-Final Office Action mailed Sep. 25, 2007, 7 pgs.
U.S. Appl. No. 11/422,418, Non-Final Office Action mailed Sep. 15, 2008, 11 pgs.
U.S. Appl. No. 11/422,418, Response filed Dec. 15, 2008 to Non-Final Office Action mailed Sep. 15, 2008, 12 pgs.
U.S. Appl. No. 11/422,418, Response filed Apr. 27, 2009 to Restriction Requirement mailed Mar. 25, 2009, 6 pgs.
U.S. Appl. No. 11/422,418, Restriction Requirement mailed Mar. 25, 2009, 7 pgs.
U.S. Appl. No. 11/422,418, Non-Final Office Action mailed Aug. 13, 2009, 8 pgs.
U.S. Appl. No. 11/422,418, Notice of Allowance mailed Jan. 28, 2010, 8 pgs.
U.S. Appl. No. 11/422,418, Response filed Nov. 13, 2009 to Non-Final Office Action mailed Aug. 13, 2009, 7 pgs.
U.S. Appl. No. 11/422,421, Non-Final Office Action mailed Dec. 10, 2008, 16 pgs.
U.S. Appl. No. 11/422,421, Final Office Action mailed Jul. 22, 2009, 15 pgs.
U.S. Appl. No. 11/422,421, Response filed Apr. 9, 2009 to Non-Final Office Action mailed Dec. 10, 2008, 12 pgs.
U.S. Appl. No. 11/422,421, Response filed Sep. 17, 2009 to Final Office Action mailed Jul. 22, 2009, 9 pgs.
U.S. Appl. No. 11/422,423, Non-Final Office Action mailed Jan. 10, 2008, 10 pgs.
U.S. Appl. No. 11/422,423, Non-Final Office Action mailed Oct. 8, 2008, 9 pgs.
U.S. Appl. No. 11/422,423, Response filed May 12, 2008 to Non-Final Office Action mailed Jan. 10, 2008, 12 pgs.
U.S. Appl. No. 11/422,423, Non-Final Office Action mailed Jun. 1, 2009, 7 pgs.
U.S. Appl. No. 11/422,423, Response filed Feb. 9, 2009 to Non-Final Office Action mailed Oct. 8, 2008, 8 pgs.
U.S. Appl. No. 11/422,423, Response filed Sep. 1, 2009 to Non Final Office Action mailed Jun. 1, 2009, 8 pgs.
U.S. Appl. No. 11/752,377, Response filed Aug. 10, 2009 to Restriction Requirement mailed Jul. 9, 2009, 6 pgs.
U.S. Appl. No. 11/752,377, Response filed Oct. 8, 2009 to Restriction Requirement, mailed Sep. 9, 2009, 5 pgs.
U.S. Appl. No. 11/752,377, Restriction Requirement mailed Sep. 9, 2009, 9 Pgs.
European Application Serial No. 07782375.5, Communication mailed Aug. 10, 2009, 4 pgs.
European Application Serial No. 07797400.4, Communication mailed Apr. 21, 2009, 3 pgs.
International Application No. PCT/US2007/018631, International Search Report mailed Mar. 25, 2008, 4 pgs.
International Application No. PCT/US2007/018631, Written Opinion mailed Mar. 25, 2008, 7 pgs.
International Application Serial No. PCT/US2007/06178, International Search Report mailed Oct. 31, 2007, 5 pgs.
International Application Serial No. PCT/US2007/06178, Written Opinion mailed Oct. 31, 2007, 8 pgs.
PCT Application No. PCT/US2007/068617, International Search Report mailed Mar. 10, 2008, 4 pgs.
PCT Application No. PCT/US2007/068617, Written Opinion mailed Mar. 10, 2008, 8 pgs.
Issa, Z. F., et al., "Thoracic spinal cord stimulation reduces the risk of ischemic ventricular arrhythmias in a postinfarction heart failure canine model", *Circulation*, 111(24), (Jun. 21, 2005), 3217-3220.
Knott, E. M., et al., "Increased lymphatic flow in the thoracic duct during manipulative intervention", *J Am Osteopath Assoc.*, 105(10), (Oct. 2005), 447-456.
Lei, Y., et al., "Effects and Mechanisms of Implantable Gastric Stimulation on Gastric Distention in Conscious Dogs", *Obesity Surgery*, 15(4), (Apr. 2005), 528-533.
Pulley, M. S., et al., "Intravenous, intralesional and endolymphatic administration of lymphokines in human cancer", *Lymphokine Research.*, 5(Supp. 1), (1986), S157-S163.
Sobotta, J, et al., „Atlas of Human Anatomy, vol. III, W.B. Sauder Company, (2006), 274-275.
U.S. Appl. No. 11/422,423, Decision on Pre-Appeal Brief Request mailed May 24, 2011, 2 pgs.
U.S. Appl. No. 11/422,423, Notice of Allowance mailed Jul. 6, 2011, 9 pgs.
U.S. Appl. No. 11/422,423, Notice of Allowance mailed Oct. 18, 2011, 5 pgs.

(56) References Cited

OTHER PUBLICATIONS

U.S. Appl. No. 11/422,423, Pre-Appeal Brief Request filed Apr. 11, 2011, 5 pgs.
U.S. Appl. No. 11/469,793, Response filed Jul. 14, 2011 to Final Office Action mailed Mar. 14, 2011, 7 pgs.
U.S. Appl. No. 11/752,377, Response filed Mar. 5, 2012 to Final Office Action mailed Oct. 4, 2011, 6 pgs.
U.S. Appl. No. 11/752,377, Final Office Action mailed Aug. 15, 2012, 10 pgs.
U.S. Appl. No. 11/752,377, Final Office Action mailed Oct. 4, 2011, 8 pgs.
U.S. Appl. No. 11/752,377, Non Final Office Action mailed Mar. 30, 2012, 9 pgs.
U.S. Appl. No. 11/752,377, Response filed Jul. 11, 2012 to Non Final Office Action mailed Mar. 30, 2012, 6 pgs.
U.S. Appl. No. 11/752,377, Response filed Jul. 25, 2011 to Non Final Office Action mailed Mar. 23, 2011, 6 pgs.
U.S. Appl. No. 12/430,211, Non Final Office Action mailed Mar. 23, 2011, 16 pgs.
U.S. Appl. No. 12/430,211, Appeal Brief filed Aug. 8, 2012 t, 9 pgs.
U.S. Appl. No. 12/430,211, Final Office Action mailed Dec. 9, 2011, 6 pgs.
U.S. Appl. No. 12/430,211, Response filed Oct. 21, 2011 to Non Final Office Action mailed Jun. 23, 2011, 8 pgs.
U.S. Appl. No. 12/604,233 , Response filed Jul. 9, 2012 to Non Final Office Action mailed Apr. 10, 2012, 14 pgs.
U.S. Appl. No. 12/604,233, Non Final Office Action mailed Apr. 10, 2012, 14 pgs.
U.S. Appl. No. 12/604,233, Response filed Jun. 15, 2011 to Advisory Action mailed May 3, 2011, 13 pgs.
Australian Application Serial No. 2007293445, First Examiners Report mailed Apr. 11, 2012, 1 pg.
Japanese Application Serial No. 2009-514438, Office Action mailed Feb. 27, 2012, (w/ English Translation), 5 pgs.
Japanese Application Serial No. 2009-514438, Response filed May 25, 2012 to Office Action mailed Feb. 27, 2012, (w. English Translation of Amended Claims), 10 pgs.
Japanese Application Serial No. 2009-514441, Office Action mailed Feb. 29, 2012, (w/ English Translation), 6 pgs.
U.S. Appl. No. 12/430,211, Examiners Answer to Appeal Brief mailed Nov. 9, 2012, 8 pgs.
U.S. Appl. No. 12/430,211, Reply Brief filed Jan. 9, 2013, 24 pgs.
U.S. Appl. No. 12/604,233, Notice of Allowance mailed Oct. 3, 2012, 11 pgs.
Japanese Application Serial No. 2009-514438, Office Action mailed Nov. 19, 2012, With English Translation, 3 pgs.
Application Serial No. 2009-514438, Response filed Feb. 8, 2013 to Non Final Office Action dated Nov. 19, 2012, With English Claims, 9.
U.S. Appl. No. 11/675,696, Response filed Jul. 1, 2009 to Restriction Requirement mailed Jun. 2, 2009, 6 pgs.
U.S. Appl. No. 11/422,414, Non-Final Office Action mailed May 27, 2010, 10 pgs.
U.S. Appl. No. 11/422,414, Notice of Allowance mailed Oct. 13, 2010, 7 pgs.
U.S. Appl. No. 11/422,414, Response filed Aug. 26, 2010 to Non Final Office Action mailed May 27, 2010, 6 pgs.
U.S. Appl. No. 11/422,417—Notice of Allowance mailed Dec. 12, 2008, 4 pgs.
U.S. Appl. No. 11/422,417—Restriction Requirement mailed Jul. 25, 2007, 5 pgs.
U.S. Appl. No. 11/422,417, Response filed Aug. 27, 2007 to Restriction Requirement mailed Jul. 25, 2007, 4 pgs.
U.S. Appl. No. 11/422,417, Restriction Requirement mailed Jul. 25, 2007, 5 pgs.
U.S. Appl. No. 11/422,421, Advisory Action mailed Sep. 28, 2009, 5 pgs.
U.S. Appl. No. 11/422,423 , Non-Final Office Action mailed Nov. 30, 2009., 11 pgs.
U.S. Appl. No. 11/422,423 Non-Final Office Action mailed Jul. 21, 2010, 13 pgs.
U.S. Appl. No. 11/422,423, Final Office Action mailed Apr. 9, 2010, 12 pgs.
U.S. Appl. No. 11/422,423, Final Office Action mailed Dec. 10, 2010, 13 pgs.
U.S. Appl. No. 11/422,423, Response filed Nov. 22, 2010 to Non Final Office Action maield Jul. 21, 2010, 11 pgs.
U.S. Appl. No. 11/422,423, Response filed Jul. 8, 2010 to Final Office Action mailed Apr. 9, 2010, 9 pgs.
U.S. Appl. No. 11/469,793 Non-Final Office Action mailed Sep. 30, 2010, 9 pgs.
U.S. Appl. No. 11/469,793, Non-Final Office Action mailed Mar. 12, 2010, 6 pgs.
U.S. Appl. No. 11/469,793, Response filed Dec. 22, 2010 to Non Final Office Action mailed Sep. 30, 2010, 7 pgs.
U.S. Appl. No. 11/469,793, Response filed Jul. 12, 2010 to Non Final Office Action mailed Mar. 12, 2010, 10 pgs.
U.S. Appl. No. 11/675,696, Non-Final Office Action mailed Sep. 30, 2009, 8 pgs.
U.S. Appl. No. 11/675,696, Response filed Dec. 28, 2009 to Non Final Office Action mailed Sep. 30, 2009, 8 pgs.
U.S. Appl. No. 11/675,696, Restriction Requirement mailed Jun. 2, 2009, 8 pgs.
U.S. Appl. No. 11/752,377 Non-Final Office Action mailed Nov. 27, 2009, 11 pgs.
U.S. Appl. No. 11/752,377, Final Office Action mailed May 26, 2010, 9 pgs.
U.S. Appl. No. 11/752,377, Notice of Non-Compliant Amendment mailed Oct. 23, 2009, 3 pgs.
U.S. Appl. No. 11/752,377, Response filed Feb. 25, 2010 to Non Final Office Action mailed Nov. 27, 2009, 5 pgs.
U.S. Appl. No. 11/752,377, Response filed Nov. 17, 2009 to Notice of Non Compliant mailed Oct. 23, 2009, 5 pgs.
U.S. Appl. No. 11/752,377, Response filed Aug. 26, 2010 to Final Office Action mailed May 26, 2010, 8 pgs.
U.S. Appl. No. 11/752,377, Restriction Requirement mailed Jul. 9, 2009, 6 pgs.
U.S. Appl. No. 12/430,211 Non-Final Office Action mailed Sep. 1, 2010, 11 pgs.
U.S. Appl. No. 12/430,211, Final Office Action mailed Feb. 1, 2011, 13 pgs.
U.S. Appl. No. 12/430,211, Response filed Jan. 3, 2011 to Non Final Office Action mailed Sep. 1, 2010, 10 pgs.
U.S. Appl. No. 12/604,233 Non-Final Office Action mailed Sep. 16, 2010, 10 pgs.
U.S. Appl. No. 12/604,233, Final Office Action mailed Feb. 15, 2011, 9 pgs.
U.S. Appl. No. 12/604,233, Response filed Dec. 16, 2010 to Non Final Office Action mailed Sep. 16, 2010, 12 pgs.
European Application No. 07797264.1, Office Action Mailed Jan. 20, 2010, 3 pgs.
European Application No. 07797264.1, Response filed Apr. 28, 2010 to Office Action Mailed Jan. 20, 2010, 13 pgs.
European Application Serial No. 07782375.5, Office Action mailed Nov. 22, 2010, 5 pgs.
European Application Serial No. 07782375.5, Response filed Feb. 15, 2010 to Communication mailed Aug. 10, 2009, 8 pgs.
European Application Serial No. 07797400.4, European Office Action mailed Aug. 13, 2010, 4 pgs.
European Application Serial No. 07797400.4, Response filed Oct. 12, 2009 to Communication mailed Apr. 21, 2009, 10 pgs.
Japanese Application Serial No. 2009-514448, Amended Claims filed Feb. 6, 2009, (w/ English Translation of Claims), 9 pgs.
"Physician's Manual—VNS Therapy tm Lead Model 302", Copyright 2003, 2004, 2005 Cyberonics, Inc., Houston, TX, (Jul. 2005), 35 pgs.
U.S. Appl. No. 11/675,696, Response to Notice of Non-Compliant Amendment, 3 pgs, Feb. 10, 2010.
Gray, H., et al., "2. The Thoractic Duct", Anatomy of the Human Body, Philadelphia: Lea & Febiger,, [online]. Bartleby.com 2000. Retrieved from the Internet: <URL: www.bartleby.com/107>, (1918), 3 pgs.
Yimtae, K., et al., "Connection between the inner ear and the lymphatic system", Laryngoscope, 111(9), (Sep. 2001), 1631-5.

* cited by examiner

METHOD AND APPARATUS FOR GASTROINTESTINAL STIMULATION VIA THE LYMPHATIC SYSTEM

CROSS-REFERENCE TO RELATED APPLICATIONS

This application is a divisional of U.S. application Ser. No. 11/422,418, filed Jun. 6, 2006, now issued as U.S. Pat. No. 7,734,341, which is hereby incorporated by reference in its entirety.

This application is related to commonly assigned, U.S. patent application Ser. No. 11/422,423, entitled "METHOD AND APPARATUS FOR LYMPHATIC SYSTEM PACING AND SENSING," filed on Jun. 6, 2006, now issued as U.S. Pat. No. 8,126,538, U.S. patent application Ser. No. 11/422,421, entitled "METHOD AND APPARATUS FOR NEURAL STIMULATION VIA THE LYMPHATIC SYSTEM," filed on Jun. 6, 2006, now abandoned, U.S. patent application Ser. No. 11/422,417, entitled "METHOD AND DEVICE FOR LYMPHATIC SYSTEM MONITORING," filed on Jun. 6, 2006, now issued as U.S. Pat. No. 7,526,337, and U.S. patent application Ser. No. 11/422,414, entitled "METHOD AND DEVICE FOR ENDO-LYMPHATIC STIMULATION," filed on Jun. 6, 2006, now issued as U.S. Pat. No. 7,894,906, which are hereby incorporated herein by reference in their entirety.

TECHNICAL FIELD

This document relates generally to medical devices and particularly to an implantable system that delivers gastrointestinal (GI) stimulation via one or more lymphatic vessels.

BACKGROUND

Electrical stimulation has been applied to treat digestive disorders and control body weight. Such electrical stimulation includes delivering stimulation pulses to the organs or nerves of the gastrointestinal (GI) tract, such as the stomach or vagus nerves that regulate functions of the stomach. For example, to treat morbid obesity associated with compulsive overeating, electrical stimuli are delivered to the vagus nerves or the stomach to create a sensation of satiety (fullness). The stimulation results in loss of desire to eat in a patient with obesity associated with overeating. When the patient's natural biofeedback fails to properly regulate his or her eating behavior, the electrical stimulation may provide an effective feedback control that discourages consumption of food in excessive quantities.

Implantable medical systems have been used to deliver electrical stimulation to treat obesity. A typical implantable electrical stimulation system includes an implantable stimulator that delivers electrical stimulation pulses through a plurality of stimulation electrodes. Depending on the location of the target structure to be stimulated, the stimulation electrodes may be incorporated onto the implantable stimulator and/or connected to the implantable stimulator using one or more implantable leads. The procedure of device implantation involves a certain level of risk associated with factors including the degree of invasiveness and anatomical complexity of each desirable stimulation site. The desirable stimulation site may not be in or near a location with an anatomical structure allowing for easy implantation of the implantable stimulator and/or the lead(s). Therefore, given a desirable stimulation site for obesity control, there is a need to minimize the invasiveness of implanting a system that delivers stimuli to that stimulation site.

SUMMARY

An implantable gastrointestinal (GI) stimulation system includes an implantable medical device coupled to at least one stimulus delivery device configured to be placed in one or more lymphatic vessels of a patient, such as the patient's thoracic duct and/or vessels branching from the thoracic duct. In one embodiment, to control obesity, GI stimuli are delivered from the stimulus delivery device to organs and/or nerves of the GI tract to create a sensation of satiety and/or to expedite food movement through the GI tract.

In one embodiment, a GI system includes an electrode assembly and an implantable medical device. The electrode assembly includes an electrode base configured to be implanted into a lymphatic vessel and a stimulation electrode on the electrode base. The electrode base is configured to cause a portion of the lymphatic vessel to substantially alter its natural path to contact a target region to which GI stimuli are delivered and maintain the contact between the portion of the lymphatic vessel and the target region after the implantation of the electrode assembly. The implantable medical device includes a GI stimulation circuit and an implant control circuit. The GI stimulation circuit delivers the GI stimuli through the stimulation electrode. The implant control circuit controls the delivery of the GI stimuli using a plurality of stimulation parameters selected to stimulate one or more of the organs and/or nerves of the GI tract.

In one embodiment, a method for delivering GI stimulation is provided. GI stimuli are delivered to one or more of the organs and/or nerves of the GI tract from an implantable medical device through at least one stimulation electrode placed in a lymphatic vessel.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
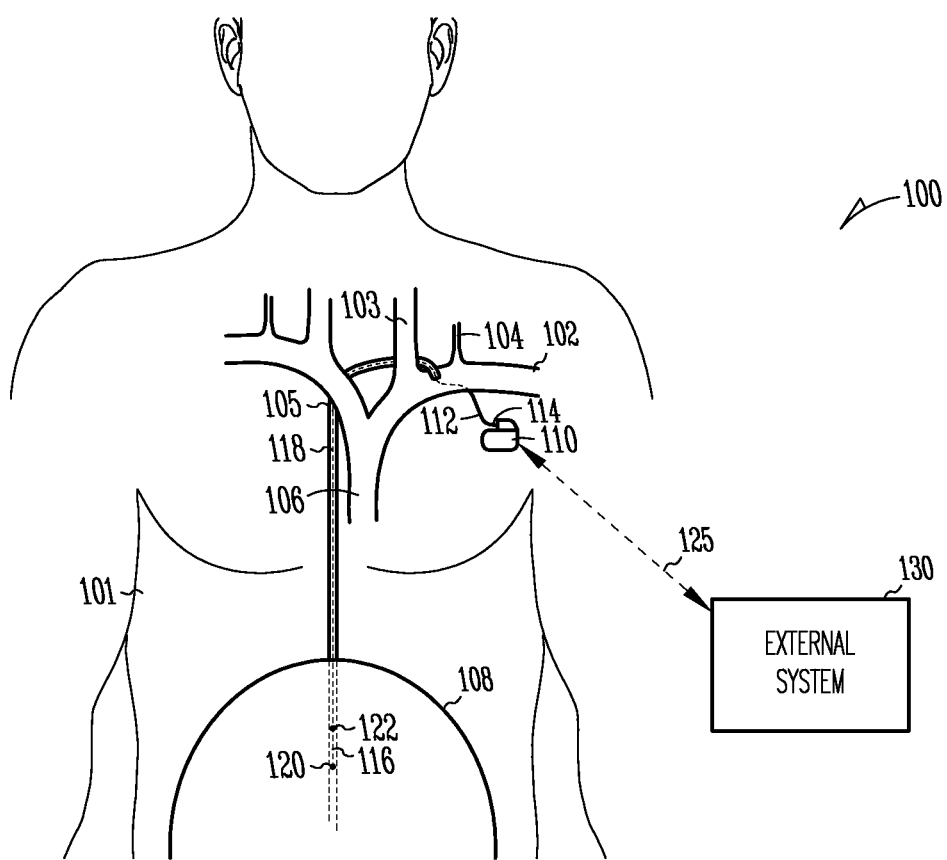
FIG. 1 is an illustration of an embodiment of a gastrointestinal (GI) stimulation system for obesity control and portions of an environment in which the GI stimulation system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses an implantable gastrointestinal (GI) stimulation system. The implantable GI stimulation system includes an implantable medical device and at least one stimulus delivery device placed a lymphatic vessel, such as the thoracic duct, of a patient. The implantable medical device delivers GI stimuli to one or more organs and/or nerves of the GI tract (i.e., GI organs and nerves innervating the GI organs) through the stimulus delivery device placed in the lymphatic vessel. In one embodiment, the implantable GI stimulation system includes a transluminal lead configured for insertion into a portion of the lymphatic vessel to allow one or more stimulation electrodes to be placed in the lymphatic vessel. The implantable medical device includes a GI stimulation circuit that generates electrical stimulation pulses. The electrical stimulation pulses are delivered to one or more target regions adjacent to the lymphatic vessel through the one or more stimulation electrodes placed in the thoracic duct. While the thoracic duct is specifically discussed in this document as an example of such a lymphatic vessel, the GI stimuli are delivered through any one or more lymphatic vessels, including, but not limited to, the thoracic duct, lymphatic vessels branching from the thoracic duct, the right lymphatic duct, and lymphatic vessels branching from the right lymphatic duct.

The implantable GI stimulation system allows for obesity control by using electrical stimulation to adjust the patient's eating behavior and/or digestive activities. In one embodiment, one or more target regions and parameters are selected to create a sensation of satiety in the patient. Examples of such target regions include the vagus nerves and the sensory receptors in the stomach. The sensation of satiety is transmitted to the brain through afferent sensory fibers in the vagus nerves. In another embodiment, one or more target regions and parameters are selected to regulate the GI motor functions for a quicker movement of food through the GI tract to reduce alimentary absorption. Examples of such target regions include the enteric nerves of the GI tract, which control GI motor and secretive functions, and the vagus nerves, which regulate gastric motor and secretive functions. In another embodiment, one or more target regions and parameters are selected to create a sensation of satiety while expediting the movement of food through the GI tract.

While electrical stimulation is specifically discussed in this document as an example, various embodiments of the GI stimulation include stimulation of the organs and/or nerves of the GI tract using any form of energy. While electrical stimulation pulses are specifically discussed as the GI stimuli, various embodiments of the GI stimulation may use electrical or non-electrical stimuli. In various embodiments, the stimulus delivery device placed in the thoracic duct generates or receives the GI stimuli, which are then delivered to one or more stimulation sites via the thoracic duct. The GI stimuli are in one or more forms of energy such as electrical, magnetic, electromagnetic, and/or acoustic (including ultrasonic) energies.

While the GI stimulation for obesity control is specifically discussed in this document, the present subject matter generally provides method and apparatus for stimulation of one or more organs and/or nerves of the GI tract via the thoracic duct. Various embodiments of the GI stimulation are not limited to applications in obesity control. For example, by selecting suitable stimulation sites and parameters, the present subject matter provides GI stimulation for treatment of gastroparesis by delivering stimuli to one or more organs and/or nerves of the GI tract using one or more stimulus delivery devices such as electrodes placed in the thoracic duct. Gastroparesis is a digestive disorder in which the normal gastrointestinal motor functions are impaired, resulting in prolonged movement of food through the GI system and, consequently, reduced food consumption in unhealthily low quantities.

FIG. 1 is an illustration of an embodiment of a GI stimulation system 100 and portions of an environment in which system 100 is used. System 100 includes an implantable medical device 110, a lead 112, an external system 130, and a telemetry link 125 providing for communication between implantable medical device 110 and external system 130. In various embodiments, system 100 delivers GI stimuli, including electrical stimulation pulses, to one or more organs and/or nerves of a GI tract 108. The nerves of GI tract 108 include nerves in GI tract 108 and nerves connected to GI tract 108 to regulate functions thereof.

In the embodiments specifically discussed below, system 100 delivers GI stimuli, which are electrical stimulation pulses, through at least one electrode placed in a thoracic duct 105, which is part of the lymphatic system of a patient's body 101. The lymphatic system includes lymph tissue, nodes, and vessels. Interstitial fluid is absorbed from tissue, filtered through lymph nodes, and empties into lymphatic vessels. FIG. 1 illustrates portions of thoracic duct 105, a subclavian vein 102, a left external jugular vein 104, a left internal jugular vein 103, and a superior vena cava 106. Thoracic duct 105 connects to the venous system at the juncture of subclavian vein 102 and a left internal jugular vein 103. The fluid (lymph) from the lower body flows up to thoracic duct 105 and empties into subclavian vein 102 from thoracic duct 105. Thoracic duct 105 is located in the posterior mediastinal and abdominal area of body 101, adjacent to portions of the GI organs and nerves innervating the GI organs. Electrical stimulation of these organs and/or nerves is delivered by using one or more stimulation electrodes placed within thoracic duct 105. Thoracic duct 105 is used as a conduit for advancing the one or more stimulation electrodes to one or more locations from which electrical stimulation can be delivered to one or more target regions in body 101. The one or more targets regions include one or more of the organs and nerves of GI tract 108. In various embodiments, the electrical stimulation is delivered to one or more the GI organs, including the stomach and the intestines, and nerves innervating GI tract 108, including the parasympathetic nerves, the sympathetic nerves, and the enteric nerves. The approach to the process of electrode placement for GI stimulation via thoracic duct 105 has the potential of reducing the invasiveness of implantation procedure under many circumstances.

Implantable medical device 110 generates the GI stimuli and delivers the GI stimuli through lead 112. In one embodiment, implantable medical device 110 also senses signals indicative of digestive activities, such as neural signals in the nerves of GI tract 108, using lead 112. In various embodiments, implantable medical device 110 is capable of sensing other physiological signals and/or delivering therapies in addition to the GI stimulation. Examples of such additional therapies include neural stimulation therapy, cardiac pacing therapy, cardioversion/defibrillation therapy, cardiac resynchronization therapy (CRT), cardiac remodeling control therapy (RCT), drug therapy, cell therapy, and gene therapy. In various embodiments, implantable medical device 110 delivers the GI stimulation in coordination with one or more such additional therapies. In one embodiment, in addition to lead 112, system 100 includes one or more endocardial and/or epicardial leads for delivering pacing and/or defibrillation pulses to the heart. In one embodiment, system 100 also delivers neural stimulation pulses to restore, regulate, or inhibit non-digestive functions. The combination of the GI stimulation with one or more other therapies is valuable because obesity is known to be associated with a variety of pathological conditions.

Lead 112 is an implantable electrical stimulation lead including a proximal end 114, a distal end 116, and an elongate lead body 118 between proximal end 114 and distal end 116. Proximal end 114 is coupled to implantable medical device 110. Distal end 116 includes at least one stimulation electrode for delivering the GI stimuli to a target region. In one embodiment, as illustrated in FIG. 1, distal end 116 includes stimulation electrodes 120 and 122. In various other embodiments, distal end 116 includes one stimulation electrode or three or more stimulation electrodes. In one embodiment, a reference electrode is incorporated onto implantable medical device 110. In a specific embodiment, implantable medical device 110 includes a hermetically sealed conductive housing that functions as the reference electrode. GI stimuli are delivered using (i) two stimulation electrodes in distal end 116 (electrodes 120 or 122), or (ii) a stimulation electrode (electrode 120 or 122) in distal end 116 and the reference electrode on implantable medical device 110. In various embodiments, one or more of the stimulation electrodes are also used for sensing one or more signals indicative of sensory and/or motor activities associated with GI tract 108. The distal portion of elongate lead body 118 (a substantial portion of elongate lead body 118 coupled to distal end 116) is configured for placement in subclavian vein 102 and thoracic duct 105, such that distal end 116 is placed in thoracic duct 105. During the implantation of lead 112, distal end 116 is inserted into subclavian vein 102 through an incision, advanced in subclavian vein 102 toward thoracic duct 105, inserted into thoracic duct 105 from subclavian vein 102, and advanced in thoracic duct 105 until a predetermined location in thoracic duct 105 is reached. In one embodiment, the position of distal end 116 is adjusted by delivering test GI stimuli and detecting the anticipated physiological responses. In one embodiment, lead 112 includes a fixation mechanism configured to stabilize distal end 116 in the determined position in thoracic duct 105. Implantable medical device 110 is connected to proximal end 114 and is subcutaneously implanted. One example of method and apparatus for accessing the lymphatic system is discussed in U.S. patent application Ser. No. 11/422,423, entitled "METHOD AND APPARATUS FOR LYMPHATIC SYSTEM PACING AND SENSING," filed on even data herewith, assigned to Cardiac Pacemakers, Inc., which is incorporated herein by reference in its entirety. Specific examples of electrode configurations and placement are also discussed in detail below, with reference to FIGS. 9-13.

In one embodiment, lead 112 is configured such that distal end 116 can be further advanced into a lymphatic vessel branching from thoracic duct 105, such as the gastric branch, so that the stimulation electrode can be placed in close proximity of a desirable target region. After the distal end 116 is inserted into thoracic duct 105, it is advanced to the junction of thoracic duct 105 and the branching lymphatic vessel and inserted to the branching lymphatic vessel. While the placement of at least one stimulation electrode in the thoracic duct is specifically discussed as an example of providing for access to a target region, the present subject matter generally includes introducing one or more stimulus delivery devices such as one or more stimulation electrodes to a target region via a lymphatic vessel. In various embodiments, GI stimuli are delivered through one or more stimulation electrodes placed in the lymphatic vessel and/or one or more stimulation electrodes placed in a structure that is accessible through the lymphatic vessel, including another lymphatic vessel branching from the lymphatic vessel.

In one embodiment, system 100 includes two or more leads each including one or more stimulation electrodes arranged to be placed in thoracic duct 105. In another embodiment, system 100 includes a lead with a plurality of electrodes arranged for delivering independently controllable GI stimuli to two or more target regions.

External system 130 communicates with implantable medical device 110 and provides for access to implantable medical device 110 by a physician or other caregiver. In one embodiment, external system 130 includes a programmer. In another embodiment, external system 130 is a patient management system including an external device communicating with implantable medical device 110 via telemetry link 125, a remote device in a relatively distant location, and a telecommunication network linking the external device and the remote device. The patient management system allows access to implantable medical device 110 from a remote location, for purposes such as monitoring patient status and adjusting therapies. In one embodiment, telemetry link 125 is an inductive telemetry link. In another embodiment, telemetry link 125 is a far-field radio-frequency (RF) telemetry link. Telemetry link 125 provides for data transmission from implantable medical device 110 to external system 130. This includes, for example, transmitting real-time physiological data acquired by implantable medical device 110, extracting physiological data acquired by and stored in implantable medical device 110, extracting patient history data such as occurrences of predetermined types of pathological events and therapy deliveries recorded in implantable medical device 110, and/or extracting data indicating an operational status of implantable medical device 110 (e.g., battery status and lead impedance). Telemetry link 125 also provides for data transmission from external system 130 to implantable medical device 110. This includes, for example, programming implantable medical device 110 to acquire physiological data, programming implantable medical device 110 to perform at least one self-diagnostic test (such as for a device operational status), and/or programming implantable medical device 110 to deliver one or more therapies and/or to adjust the delivery of one or more therapies.

Figure 2:
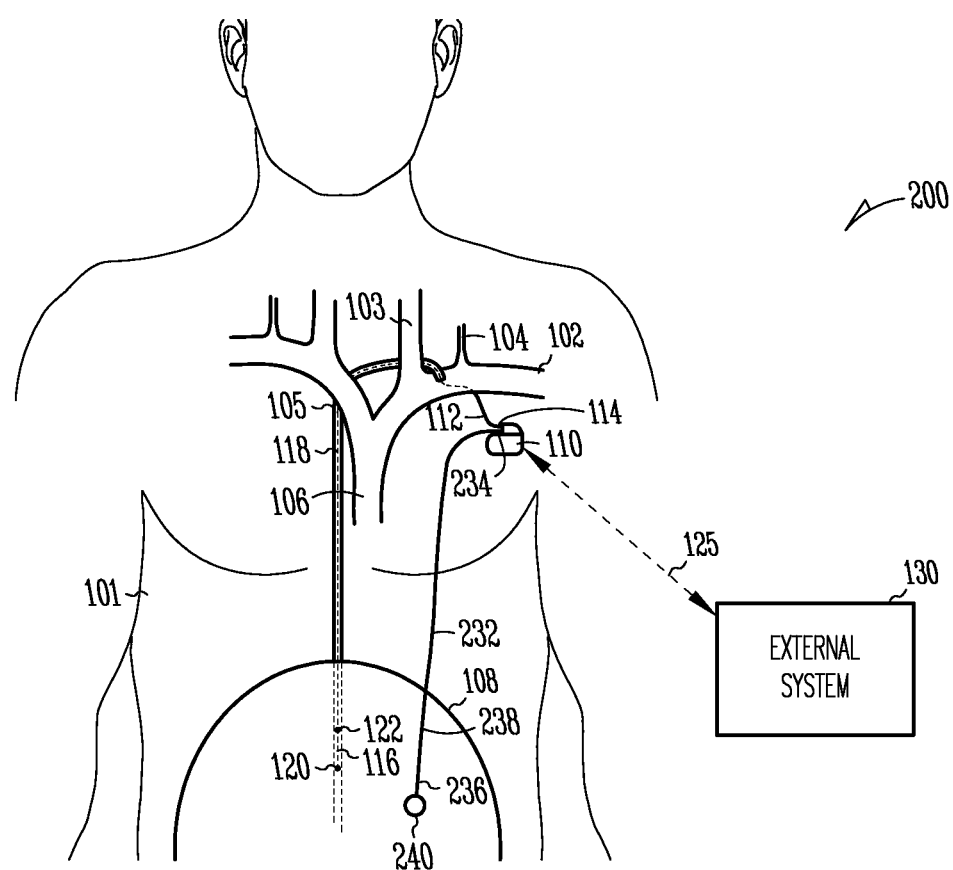
FIG. 2 is an illustration of another embodiment of the GI stimulation system and portions of the environment in which the GI stimulation system is used.

FIG. 2 is an illustration of an embodiment of a GI stimulation system 200 and portions of the environment in which system 200 is used. System 200 includes the components of GI stimulation system 100 and an additional lead 232. That is, GI stimulation system 200 includes implantable medical device 110, leads 112 and 232, external system 130, and telemetry link 125.

Lead 232 is an implantable electrical stimulation lead including a proximal end 234, a distal end 236, and an elongate lead body 238 between proximal end 234 and distal end 236. Proximal end 234 is coupled to implantable medical device 110. Distal end 236 includes at least one electrode. In one embodiment, as illustrated in FIG. 2, lead 232 includes an electrode 240 at distal end 236. In another embodiment, lead 232 includes a plurality of stimulation electrodes. In one embodiment, lead 232 is configured for subcutaneous placement, external to thoracic duct 105. In one embodiment, electrode 240 is used as a reference electrode.

Lead 232 expands the range of target regions to which the GI stimuli can be delivered from implantable medical device 110. The GI stimuli are directed by the location in body 101 where electrode 240 is subcutaneously placed. In various embodiments, GI stimuli are delivered through any pair of electrodes of system 200, including (i) two stimulation electrodes in distal end 116 (electrodes 120 and 122), (ii) a stimulation electrode in distal end 116 (electrode 120 or 122) and electrode 240 (as the reference electrode), or (iii) a stimulation electrode in distal end 116 (electrode 120 or 122) and the reference electrode on implantable medical device 110. In one embodiment, distal ends 116 and 236 are positioned such as a target structure for the GI stimulation is approximately between a stimulation electrode in distal end 116 (electrode 120 or 122) and a reference electrode (electrode 240 or the reference electrode on implantable medical device 110). This allows for stimulation of a target region not immediately adjacent to thoracic duct 105.

Figure 3:
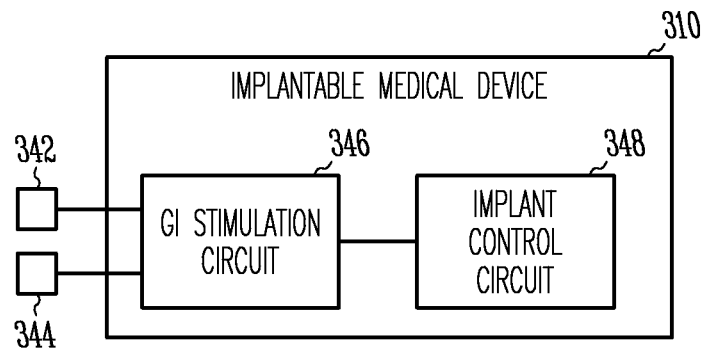
FIG. 3 is a block diagram illustrating an embodiment of an implantable medical device of the GI stimulation system.

FIG. 3 is a block diagram illustrating an embodiment of an implantable medical device 310, which is a specific embodiment of implantable medical device 110. Implantable medical device 310 includes a GI stimulation circuit 346 and an implant control circuit 348. GI stimulation circuit 346 delivers GI stimuli to a pair of stimulation electrodes 342 and 344, through which the GI stimuli are delivered to a target region in one or more nerves and/or organs of GI tract 108. At least one of stimulation electrodes 342 and 344 is placed in thoracic duct 105. Implant control circuit 348 controls the delivery of the GI stimuli from GI stimulation circuit 346.

In one embodiment, stimulation electrodes 342 and 344 are both in thoracic duct 105 and adjacent to the target region, such as electrodes 120 and 122. In another embodiment, stimulation electrode 342 is in thoracic duct 105 and adjacent to the target region, such as electrode 120 or 122, and stimulation electrode 344 is external to thoracic duct 105, such as electrode 240 or a reference electrode on implantable medical device 310. In one embodiment, the target region is approximately between stimulation electrodes 342 and 344.

Implant control circuit 348 controls the delivery of the GI stimuli from GI stimulation circuit 346 using stimulation parameters tailored to the target region and the desired response specified by the user such as a physician or other caregiver. The stimulation parameters are pre-programmed or user-programmed into implant control circuit 348. In various embodiments, the target region includes one or more regions of the GI tract that are adjacent to the thoracic duct in the abdominal region, including the nerves innervating the GI tract. Examples of the target region include one or more of the sympathetic nerves, the parasympathetic nerves (including the vagus nerves), and various locations in the stomach and intestine where the enteric nerves and sensory receptors can be activated. Examples of the desired response include one or more of a sensation of satiety, other sensations discouraging excessive food consumption, and/or an increased speed of food movement in the GI tract. Examples of the other sensations discouraging excessive food consumption include symptoms of gastroparesis (but not its actual occurrence), such as nausea, bloating, and premature or extended feeling of satiety.

For illustration purposes, FIG. 3 shows the pair of stimulation electrodes 342 and 344. In various embodiments, GI stimulation circuit 346 delivers the GI stimuli through one or more pairs of stimulation electrodes selected from a plurality of stimulation electrodes. In one embodiment, GI stimulation circuit 346 includes two or more stimulation output channels each delivering GI stimuli through a pair of stimulation electrodes. In another embodiment, an electrode array with a plurality of stimulation electrodes is placed in the thoracic duct, and one or more stimulation electrodes are selected for delivering GI stimuli by testing the physiological effect of stimulation associated with each stimulation electrode.

Figure 4:
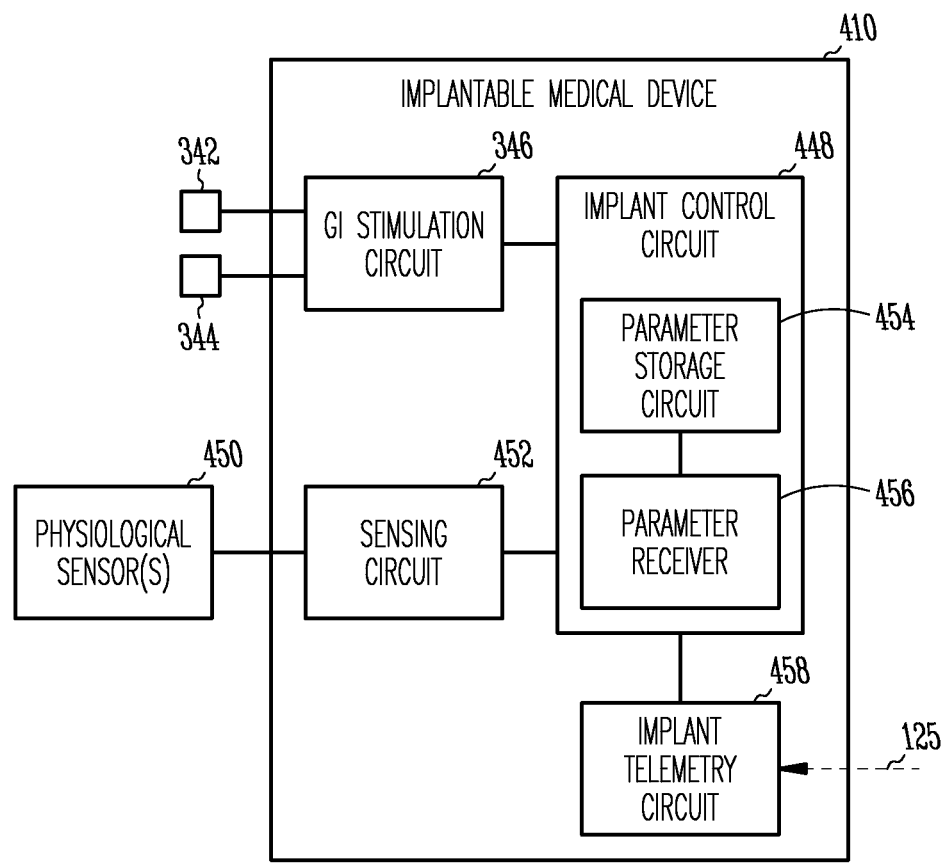
FIG. 4 is a block diagram illustrating a specific embodiment of the implantable medical device.

FIG. 4 is a block diagram illustrating an embodiment of an implantable medical device 410, which is another specific embodiment of implantable medical device 110. Implantable medical device 410 includes GI stimulation circuit 346, a sensing circuit 452, an implant control circuit 448, and an implant telemetry circuit 458. One or more physiological sensors 450 are housed within implantable medical device 410, incorporated onto implantable medical device 410, and/or connected to implantable medical device 410 using a lead.

Physiological sensor(s) 450 sense one or more physiological signals such as signals indicative of GI functions, satiety, and/or patient's various conditions associated with food consumption. Sensing circuit 452 processes the one or more physiological signals and produces signals indicative a need to start, stop, or adjust the GI stimulation. Examples of such physiological signals include neural and muscular signals indicative of mechanical activities of the GI tract, neural signals in afferent nerves transmitting the sensation of satiety to the brain, and signals indicative of blood glucose level, blood lipid level, blood pH value, and other parameters of blood chemistry. In one embodiment, physiological sensor(s) 450 include one or both of stimulation electrodes 342 and 344, which are utilized as sensing electrodes. In one embodiment, physiological sensor(s) 450 senses one or more physiological signals indicative the onset or existence of a pathological condition during which the patient's food intake should be discouraged, stopped, or regulated.

Implant control circuit 448 is a specific embodiment of implant control circuit 348 and controls the delivery of the GI stimuli from GI stimulation circuit 346 using a plurality of stimulation parameters. Implant control circuit 448 includes a parameter storage circuit 454 and a parameter receiver 456. Parameter storage circuit 454 stores values of the plurality of stimulation parameters. Examples of such stimulation parameters include pulse amplitude, pulse width, and pulse frequency (or inter-pulse interval). The values of the plurality of stimulation parameters are adjustable. Parameter receiver 456 receives values of the plurality of stimulation parameters and updates parameter storage circuit 454 with the received values. In one embodiment, implant control circuit 448 controls the delivery of the GI stimuli from GI stimulation circuit 346 by using one or more physiological signals sensed by physiological sensor(s) 450 to adjust the stimulation parameters. In various embodiments, each sensed physiological signal is used as one or more of a triggering signal to start or stop the GI stimulation, a safety assurance signal to start, stop, or adjust the intensity of the GI stimulation, and a feedback signal to provide closed-loop GI stimulation.

Implant telemetry circuit 458 transmits and receives data via telemetry link 125. In one embodiment, the values of the plurality of stimulation parameters are externally programmable, and the programmed values are received from external system 130 through telemetry link 125.

Figure 5:
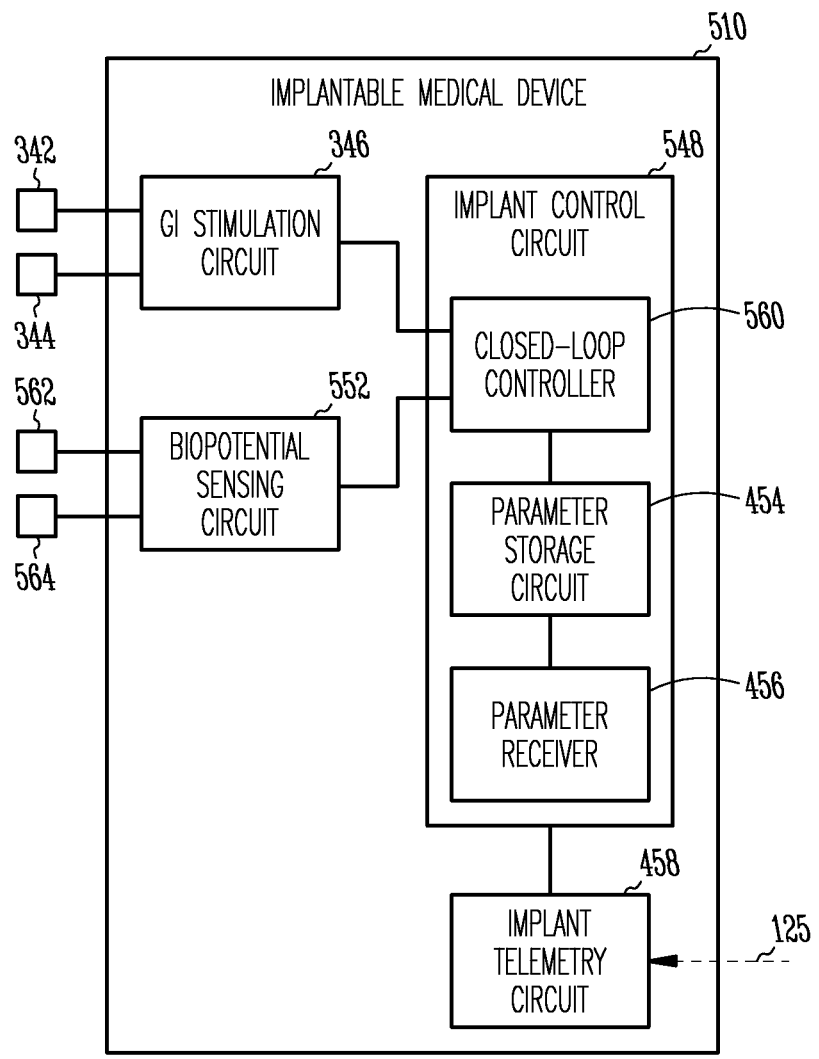
FIG. 5 is a block diagram illustrating another specific embodiment of the implantable medical device.

FIG. 5 is a block diagram illustrating an implantable medical device 510, which is a specific embodiment of implantable medical device 410. Implantable medical device 510 includes GI stimulation circuit 346, a biopotential sensing circuit 552, an implant control circuit 548, and implant telemetry circuit 458.

Biopotential sensing circuit 552 is a specific embodiment of sensing circuit 452 and processes a biopotential signal sensed using biopotential sensing electrodes 562 and 564, which represent a specific embodiment of physiological sensor(s) 450. Examples of the biopotential signal include neural signals indicative of activities in the nerves connected to the GI tract and electromyographic signals indicative of the motor activities in the GI tract. In one embodiment, biopotential sensing circuit 552 processes a neural signal indicative of a patient's condition that can be improved by regulation of food consumption and/or digestion. In one embodiment, biopotential sensing circuit 552 processes two or more biopotential signals sensed using additional biopotential sensing electrodes. In one embodiment, the biopotential signal is sensed from the same site to which the GI stimuli are delivered, and stimulation electrodes 342 and 344 are used as biopotential sensing electrodes 562 and 564. In other words, stimulation electrodes 342 and 344 and biopotential sensing electrodes 562 and 564 are physically the same pair of electrodes. In another embodiment, the biopotential signal is sensed from a site different from the site to which the GI stimuli are delivered. At least one of stimulation electrodes 342 and 344 is not used as any of biopotential sensing electrodes 562 and 564.

Implant control circuit 548 is a specific embodiment of implant control circuit controls 448 and includes a closed-loop controller 560, parameter storage circuit 454, and parameter receiver 456. Implant control circuit controls 548 controls the delivery of the GI stimuli from GI stimulation circuit 346 using a plurality of stimulation parameters and the sensed and processed biopotential signal. Closed-loop controller 560 controls the delivery of the GI stimuli using the sensed and processed biopotential signal as an input for feedback control. In one embodiment, implant control circuit controls 548 initiates the delivery of the GI stimuli when a sensed biopotential signal indicative of the patient's food intake exceeds a predetermined threshold. In another embodiment, implant control circuit 548 controls the delivery of the GI stimuli to augment the sensation of satiety when a biopotential signal indicates ongoing food consumption. In another embodiment, implant control circuit 548 initiates the delivery of the GI stimuli to augment the motor activities of the GI tract when a biopotential signal indicates ongoing food consumption and digestion. In another embodiment, implant control circuit 548 controls the delivery of the GI stimuli based on one or more biopotential signals indicative of a condition of the patient that can benefit from regulation of food consumption or ingestion.

Figure 6:
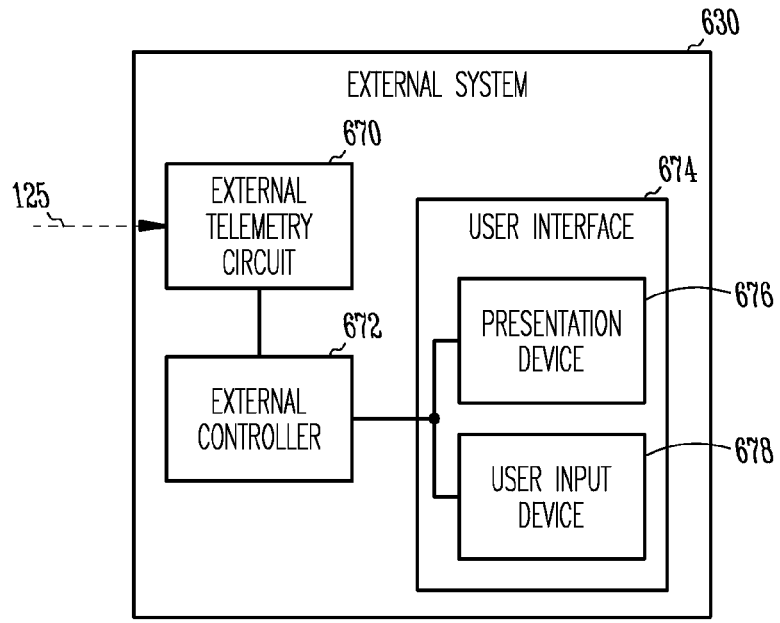
FIG. 6 is a block diagram illustrating an embodiment of an external system of the GI stimulation system.

FIG. 6 is a block diagram illustrating an embodiment of an external system 630, which is a specific embodiment of external system 130. External system 630 includes an external telemetry circuit 670, an external controller 672, and a user interface 674. External telemetry circuit 670 transmits and receives data via telemetry link 125. External controller 672 controls the operation of external system 630. User interface 674 allows a user such as a physician or other caregiver to communicate with implantable medical device 110 through external system 630. User interface 674 includes a presentation device 676 and a user input device 678. User input device 678 allows for the programming of the values of the plurality of stimulation parameters. In one embodiment, presentation device 676 and user input device 678 are integrated or partially integrated to include an interactive screen allowing for programming of implantable medical device 110.

In one embodiment, external system 630 includes a programmer. In another embodiment, external system 630 includes a patient management system as discussed below with reference to FIG. 7.

Figure 7:
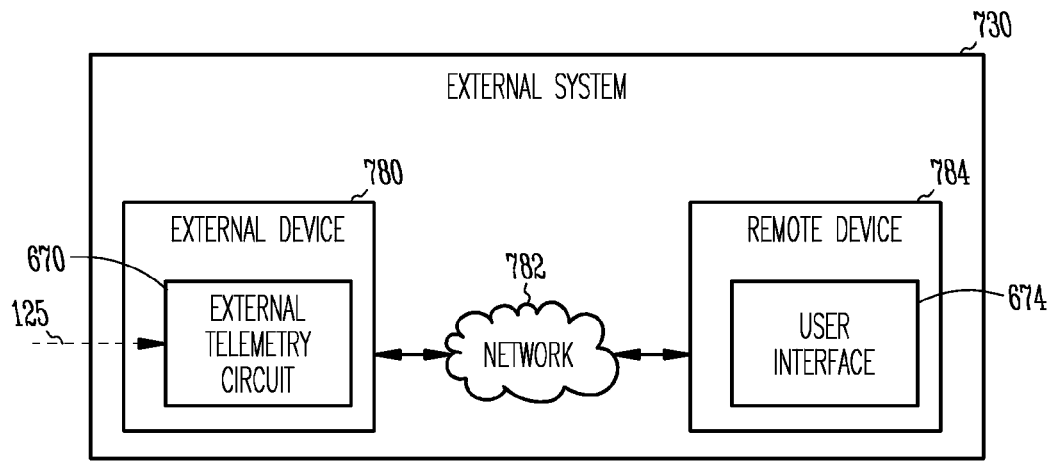
FIG. 7 is a block diagram illustrating an embodiment of the external system being a patient management system.

FIG. 7 a block diagram illustrating an embodiment of an external system 730, which is a specific embodiment of external system 630. As illustrated in FIG. 7, external system 730 is a patient management system including an external device 780, a telecommunication network 782, and a remote device 784. External device 780 is placed within the vicinity of implantable medical device 110 and includes external telemetry system 670 to communicate with the implantable medical device via telemetry link 125. Remote device 784 is in a remote location and communicates with external device 780 through network 782. Remote device 784 includes user interface 674 to allow the physician or other caregiver to monitor and treat a patient from a distant location and/or allowing access to various treatment resources from the remote location.

Figure 8:
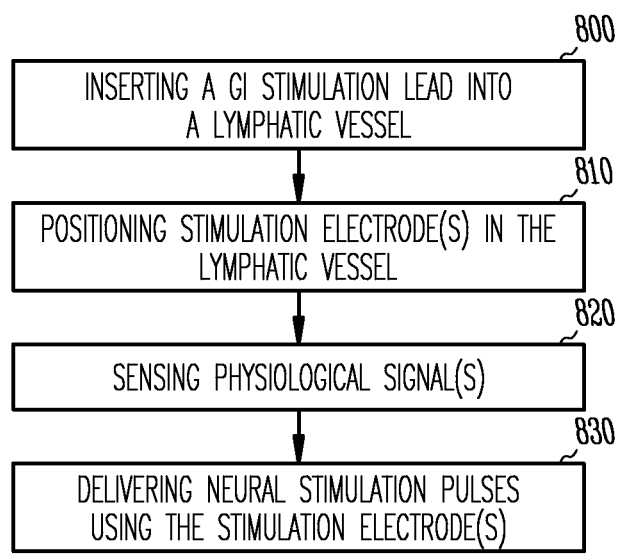
FIG. 8 is a flow chart illustrating a method for delivering GI stimulation for obesity control via the lymphatic system.

FIG. 8 is a flow chart illustrating a method for delivering GI stimulation via thoracic duct. In one embodiment, the method is performed using system 100 or system 200, including the various embodiments of their components discussed above.

A GI stimulation lead is inserted into a lymphatic vessel of a patient at 800. In one embodiment, this lymphatic vessel is the thoracic duct. The GI stimulation lead is an implantable transluminal lead having a proximal end configured for connection to an implantable medical device and a distal end including one or more stimulation electrodes. To insert the GI stimulation lead into the thoracic duct such that GI stimuli can be delivered through the stimulation electrode(s), an opening is made on the subclavian vein, upstream from the junction of the subclavian vein and the thoracic duct. The distal end of the GI stimulation lead is inserted into the subclavian vein through the opening and advanced toward the junction of the subclavian vein and the thoracic duct downstream. Then, the GI stimulation lead is guided into the thoracic duct and advanced in the thoracic duct until the distal end reaches a target region to which the GI stimuli are delivered. Examples of the target region include one or more of the nerves and organs of the GI tract adjacent to the thoracic duct, such as sympathetic nerves, parasympathetic nerves including the vagus nerve, and portions of the stomach and intestines where the enteric nerves and sensory receptors are distributed and excitable for desired responses. In one embodiment, to further approach a desirable target region, the distal end of the GI stimulation lead is guided into a lymphatic vessel branching from the thoracic duct.

The stimulation electrode(s) of the GI stimulation lead are positioned in the lymphatic vessel, such as the thoracic duct or the lymphatic vessel branching from the thoracic duct, at 810. In one embodiment, after the distal end of the GI stimulation lead reaches the region determined by the target region, test GI stimuli are delivered. The distal end is moved in the thoracic duct and/or the lymphatic vessel branching from the thoracic duct until it reaches a position identified by detecting satisfactory responses to the stimulation, such as evoked neural signals and/or other anticipated physiological effects. The distal end with the stimulation electrode(s) is then stabilized in that position.

One or more physiological signals are sensed at 820. In one embodiment, at least one physiological signal is sensed to indicate a need to start, stop, or adjust the delivery of the GI stimulation. In another embodiment, at least one physiological signal is sensed for monitoring, diagnostic, and/or therapeutic purposes other then the GI stimulation. In one embodiment, one or more neural and/or electromyographic signals are sensed. In a specific embodiment, a neural or electromyographic signal is sensed using the stimulation electrodes through which the GI stimuli are delivered. In another embodiment, one or more signals each indicative of a physiological function regulated by the GI stimulation are sensed.

GI stimuli are delivered using the stimulation electrode(s) positioned in the lymphatic vessel, such as the thoracic duct or the lymphatic vessel branching from the thoracic duct, at 830. In one embodiment, the GI stimuli are delivered through two stimulation electrodes positioned in the thoracic duct or the lymphatic vessel branching from the thoracic duct. In another embodiment, the GI stimuli are delivered using a stimulation electrode positioned in the thoracic duct or the lymphatic vessel branching from the thoracic duct and another stimulation electrode positioned in a location in the body external the lymphatic vessels. In a specific embodiment, the GI stimuli are delivered to a target region approximately between a pair of stimulation electrodes. The delivery of the GI stimuli is controlled using a plurality of stimulation parameters. Examples of the stimulation parameters include pulse amplitude, pulse width, and pulse frequency (or inter-pulse interval). These stimulation parameters are adjustable. In one embodiment, a user such as a physician or other caregiver programs one or more values of the plurality of stimulation parameters. In one embodiment, the delivery of the GI stimuli is also controlled using the one or more physiological signals. The stimulation parameters are selected such that the GI stimulation creates a sensation of satiety, other sensations discouraging overeating, and/or increased motor activities in the GI tract.

FIGS. 9-13 illustrate, by way of example, various embodiments of an electrode assembly for placement in the lymphatic vessel to allow for the GI stimulation. The electrode assembly includes one or more electrode bases. One or more stimulation electrodes are incorporated onto and/or integrated with each of the one or more electrode bases. In one embodiment, the one or more electrode bases each are formed as portion of a lead such as lead 112. In one specific embodiment, an electrode base is formed at distal end 116 of lead 112, and stimulation electrodes 120 and 122 are on that electrode base. In another specific embodiment, one or more electrode bases are formed in elongate lead body 118 of lead 112. In another embodiment, electrode bases are formed at distal end 116 and elongate lead body 118 of lead 112 to provide for delivery of the GI stimuli to multiple target regions.

Figure 9:
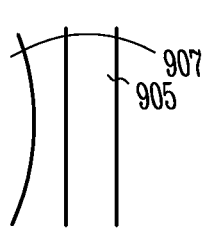
FIG. 9 is an illustration of a lymphatic vessel and a target region for GI stimulation.

FIG. 9 is an illustration of a lymphatic vessel 905 and a target region 907 in their natural state. Target region 907 is a region in the one or more organs and/or nerves of GI tract 108 to which the GI stimuli are delivered. As illustrated in FIG. 9, lymphatic vessel 905 and target region 907 are not in direct contact, or not constantly in direct contact, with each other in their natural state. Electrode assemblies illustrated in FIGS. 10-13 each cause and maintain a substantially constant and direct contact between lymphatic vessel 905 and target region 907 by substantially altering the natural path of lymphatic vessel 905. Such a substantially constant and direct contact allows for a reliable delivery of GI stimuli from one or more electrodes in lymphatic vessel 905 to target region 907. In various embodiments, lymphatic vessel 905 represents one of the thoracic duct, a vessel branching from the thoracic duct, or any lymphatic vessel suitable for placement of the one or more electrodes for the GI stimulation.

Figure 10:
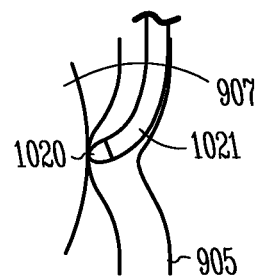
FIG. 10 is an illustration of an embodiment of an electrode assembly for placement in the lymphatic vessel to allow for the GI stimulation.

FIG. 10 is an illustration of an embodiment of an electrode assembly including an electrode base 1021 configured to be implanted in lymphatic vessel 905 and a stimulation electrode 1020 on electrode base 1021. Electrode base 1021 has an elongate shape and includes a bias configured to cause a portion of lymphatic vessel 905 to substantially alter its natural path to contact target region 907. The bias also allows electrode 1020 to be in contact with the inner wall of lymphatic vessel 905 for delivering the GI stimuli to target region 907. Electrode base 1021 has a stiffness allowing for stabilizing the position of stimulation electrode 1020 in lymphatic vessel 905 and maintaining the contact between the portion of lymphatic vessel 905 and target region 907 after implantation. In one embodiment, electrode base 1021 is in a helical form. In one embodiment, electrode base 1021 includes an elongate body having shape memory characteristics such that it returns to its preformed shape after the implantation procedure during which a stylet or guide wire may be used. The shape memory characteristics are provided by using a shape memory polymer such as polyether polyurethane or a shape memory metal. In one embodiment, the electrode assembly is coupled to implantable medical device 110 via a lead such as lead 112. In a specific embodiment, electrode base 1021 is formed at distal end 116 of lead 112, with stimulation electrode 1020 being stimulation electrode 120. In other specific embodiments, two or more stimulation electrodes are incorporated into electrode base 1021.

Figure 11:
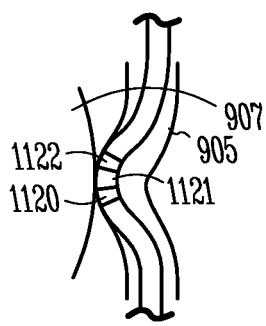
FIG. 11 is an illustration of an embodiment of another electrode assembly for placement in the lymphatic vessel to allow for the GI stimulation.

FIG. 11 is an illustration of an embodiment of another electrode assembly including an electrode base 1121 configured to be implanted in lymphatic vessel 905 and stimulation electrodes 1120 and 1122, both on electrode base 1121. Electrode base 1121 has an elongate shape and includes a bias configured to cause a portion of lymphatic vessel 905 to substantially alter its natural path to contact target region 907. The bias also allows electrodes 1120 and 1122 to be in contact with the inner wall of lymphatic vessel 905 for delivering the GI stimuli to target region 907 using either or both of electrodes 1120 and 1122. Electrode base 1121 has the stiffness allowing for stabilizing the positions of stimulation electrodes 1120 and 1122 in lymphatic vessel 905 and maintaining the contact between the portion of lymphatic vessel 905 and target region 907 after implantation. In one embodiment, electrode base 1121 is in a helical form. In one embodiment, electrode base 1121 includes an elongate body having shape memory characteristics such that it returns to its preformed shape after the implantation procedure during which a stylet or guide wire may be used. The shape memory characteristics are provided by using a shape memory polymer such as polyether polyurethane or a shape memory metal. In one embodiment, the electrode assembly is coupled to implantable medical device 110 via a lead such as lead 112. In a specific embodiment, electrode base 1121 is formed at distal end 116 of lead 112, with stimulation electrodes 1120 and 1122 being stimulation electrodes 120 and 122. In other specific embodiments, one stimulation electrode, or three or more stimulation electrodes, are incorporated into electrode base 1121.

Figure 12:
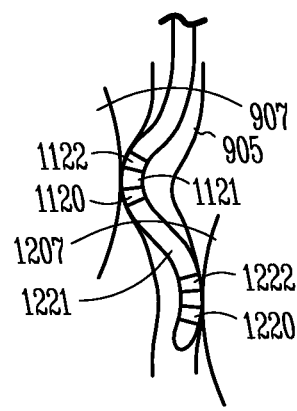
FIG. 12 is an illustration of an embodiment of another electrode assembly for placement in the lymphatic vessel to allow for the GI stimulation.

FIG. 12 is an illustration of an embodiment of another electrode assembly including an electrode base 1121 with stimulation electrodes 1120 and 1122 and another electrode base 1221 with stimulation electrodes 1220 and 1222. Electrode bases 1121 and 1221 are both configured to be implanted in lymphatic vessel 905. Electrode bases 1121 has the elongate shape and includes the bias configured to cause a portion of lymphatic vessel 905 to substantially alter its natural path to contact target region 907. The bias also allows electrodes 1120 and 1122 to be in contact with the inner wall of lymphatic vessel 905 for delivering GI stimuli to target region 907 using either or both of electrodes 1120 and 1122. Electrode bases 1221 has an elongate shape and includes a bias configured to cause a portion of lymphatic vessel 905 to substantially alter its natural path to contact a target region 1207. The bias also allows electrodes 1220 and 1222 to be in contact with the inner wall of lymphatic vessel 905 for delivering GI stimuli to target region 1207 using either or both of electrodes 1220 and 1222. Electrode bases 1121 and 1221 each have a stiffness allowing for stabilizing the positions of the stimulation electrodes in lymphatic vessel 905 and maintaining the contact between the portion of lymphatic vessel 905 and target region 907 after implantation. In one embodiment, electrode bases 1121 and 1221 are each in a helical form. In one embodiment, electrode bases 1121 and 1221 each include an elongate body having shape memory characteristics such that it returns to its preformed shape after the implantation procedure during which a stylet or guide wire may be used. The shape memory characteristics are provided by using a shape memory polymer such as polyether polyurethane or a shape memory metal. In one embodiment, the electrode assembly is coupled to implantable medical device 110 via a lead such as lead 112. In a specific embodiment, electrode base 1121 is formed at distal end 116 of lead 112, with stimulation electrodes 1120 and 1122 being stimulation electrodes 120 and 122, and electrode base 1221 is formed in elongate lead body 118 of lead 112. In other specific embodiments, one stimulation electrode, or three or more stimulation electrodes, are incorporated into each of electrode bases 1121 and 1221.

Figure 13:
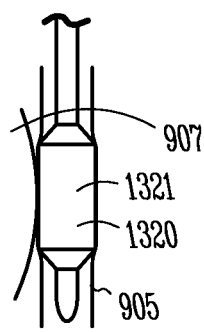
FIG. 13 is an illustration of an embodiment of another electrode assembly for placement in the lymphatic vessel to allow for the GI stimulation.

FIG. 13 is an illustration of an embodiment of another electrode assembly including an electrode base 1321 and a stimulation electrode 1320. Electrode base 1321 is expandable. After being expanded, electrode base 1321 causes a portion of lymphatic vessel 905 to substantially expand to contact target region 907. The expansion of electrode base 1321 also allows electrode 1320 to be in stable contact with the inner wall of lymphatic vessel 905 for delivering GI stimuli to target region 907. In one embodiment, electrode base 1321 includes a stent that is expanded in the lymphatic vessel to maintain patency of the vessel. In one embodiment, stimulation electrode 1320 is incorporated into the stent. In another embodiment, the stent is made of metal and functions as stimulation electrode 1320. In another embodiment, stimulation electrode 1320 is integrated into the stent to be a portion of its structure. The stent also stabilize the position of stimulation electrode 1320 in lymphatic vessel 905 and prevents obstruction of the lymphatic flow. In one embodiment, the electrode assembly is coupled to implantable medical device 110 via a lead such as lead 112. In a specific embodiment, the stent is incorporated into distal end 116 of lead 112. In another embodiment, the stent is incorporated into elongate lead body 118 of lead 112. In another embodiment, two or more stents are incorporated into elongate lead body 118 and/or distal end 116 of lead 112.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering stimulation to a target region in a body having lymphatic vessels and a gastrointestinal (GI) tract including GI organs and nerves innervating the GI organs, the target region including portions of the GI tract, the system comprising:
   a first implantable lead having a first distal end, a first proximal end, and a first elongate lead body between the first distal end and the first proximal end;
   a first electrode assembly incorporated into the first implantable lead, the first electrode assembly including a first electrode base configured to be implanted into one of the lymphatic vessels and a first stimulation electrode and a second stimulation electrode on the first electrode base away from the first distal end, the first electrode base including a bias disposed at a location of the first stimulation electrode on the first electrode base, the bias including a helix-shaped portion of the first electrode base, the bias configured to selectively cause a portion of the one of the lymphatic vessels adjacent to the target region of stimulation to substantially alter its natural path to cause the first stimulation electrode to contact the portion of the one of the lymphatic vessels with the altered natural path and maintain the contact between the portion of the one of the lymphatic vessels and the target region after an implantation of the first electrode assembly; and a second electrode base disposed at the distal end of said first implantable lead and located distally of said bias in said first electrode base; and
   an implantable medical device configured to be connected to the first proximal end of the first implantable lead, the implantable medical device including:
      a GI stimulation circuit adapted to deliver GI stimuli through the first stimulation electrode and the second stimulation electrode; and
      an implant control circuit coupled to the GI stimulation circuit, the implant control circuit adapted to control the delivery of the GI stimuli using a plurality of stimulation parameters selected to stimulate one or more of the GI organs and the nerves innervating the GI organs.

2. The system of claim 1, wherein the first electrode base comprises an elongate electrode base including the helix-shaped bias configured to cause the portion of the one of the lymphatic vessels to substantially alter its natural path to contact the target region, the elongate electrode base having a stiffness allowing for maintaining the contact between the portion of the one of the lymphatic vessels and the target region after the implantation of the first electrode assembly.

3. The system of claim 1, wherein the first electrode base further comprises an expandable electrode base configured to cause the portion of the one of the lymphatic vessels to substantially alter its natural path to contact the target region, after being expanded.

4. The system of claim 3, wherein the expandable electrode base comprises a stent, and the first electrode is incorporated into or integrated with the stent.

5. The system of claim 1, wherein the implant control circuit is programmed to include stimulation parameters selected to create a sensation discouraging food consumption.

6. The system of claim 5, wherein the implant control circuit is programmed to include stimulation parameters selected to create a sensation of satiety.

7. The system of claim 1, wherein the implant control circuit is programmed to include stimulation parameters selected to increase motor activities in the GI tract.

8. The system of claim 1, wherein the first electrode assembly is incorporated into the first elongate lead body with a spacing away from the first proximal end.

9. The system of claim 1, further comprising a second stimulation electrode configured to be placed in a location external to the lymphatic vessels, and wherein the GI stimulation circuit is adapted to deliver the GI stimuli through the first stimulation electrode and the second stimulation electrode.

10. The system of claim 9, further comprising a second implantable lead configured to be subcutaneously implanted, the second implantable lead having a second distal end including the second stimulation electrode, a second proximal end configured to be connected to the implantable medical device, and a second elongate lead body between the distal end and the proximal end.

11. The system of claim 1, further comprising a physiological sensor adapted to sense a physiological signal, and wherein the implantable medical device further comprises a sensing circuit adapted to receive and process the physiological signal, and the implant control circuit is adapted to control the delivery of the GI stimuli using the physiological signal.

12. The system of claim 11, wherein the implant control circuit comprises a closed-loop controller adapted to provide feedback control of the delivery of the GI stimuli using the physiological signal.

13. The system if claim 11, wherein the physiological sensor is adapted to sense a signal indicative of mechanical activities of the GI tract, the sensing circuit is adapted to receive and process the signal indicative of mechanical activities of the GI tract, and the implant control circuit is adapted to control the delivery of the GI stimuli using the signal indicative of mechanical activities of the GI tract.

14. The system if claim 11, wherein the physiological sensor is adapted to sense neural signals transmitting a sensation of satiety, the sensing circuit is adapted to receive and process the neural signals, and the implant control circuit is adapted to control the delivery of the GI stimuli using the neural signals.

15. The system of claim 1, further comprising biopotential sensing electrodes adapted to sense a biopotential signal, and wherein the implantable medical device further comprises a biopotential sensing circuit coupled to the biopotential sensing electrodes and adapted to process the biopotential signal, and the implant control circuit is adapted to control the delivery of the GI stimuli using the processed biopotential signal.

16. The system of claim 15, wherein the biopotential signal is indicative of food intake, and the implant control circuit is adapted to initiate the delivery of the GI stimuli when the biopotential signal exceeds a predetermined threshold.

17. The system of claim 15, wherein the implant control circuit is adapted to control the delivery of the GI stimuli to augment a sensation of satiety when the biopotential signal indicates ongoing food consumption and digestion.

* * * * *